United States Patent
Akiyoshi et al.

(10) Patent No.: US 11,938,108 B2
(45) Date of Patent: Mar. 26, 2024

(54) COMPOSITION FOR IMPROVING JOINT FUNCTION

(71) Applicant: AJINOMOTO CO., INC., Tokyo (JP)

(72) Inventors: Shinobu Akiyoshi, Kawasaki (JP); Noriko Kawasaki, Kawasaki (JP); Masako Mimura, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 16/521,029

(22) Filed: Jul. 24, 2019

(65) Prior Publication Data
US 2020/0030274 A1 Jan. 30, 2020

(30) Foreign Application Priority Data
Jul. 25, 2018 (JP) .................. 2018-139806

(51) Int. Cl.
*A61K 31/198* (2006.01)
*A61K 31/401* (2006.01)
*A61P 19/02* (2006.01)

(52) U.S. Cl.
CPC .......... *A61K 31/198* (2013.01); *A61K 31/401* (2013.01); *A61P 19/02* (2018.01)

(58) Field of Classification Search
CPC ............................. A61K 31/198; A61P 19/02
See application file for complete search history.

(56) References Cited

U.S. PATENT DOCUMENTS

| 7,645,796 | B2 * | 1/2010 | Murakami | A61K 8/44 |
| | | | | 514/561 |
| 2004/0254142 | A1 * | 12/2004 | Kovler | A61K 31/496 |
| | | | | 514/54 |
| 2007/0155666 | A1 * | 7/2007 | Alkayali | A61K 38/39 |
| | | | | 530/350 |
| 2012/0088820 | A1 * | 4/2012 | Lee | A61K 31/198 |
| | | | | 514/44 R |
| 2015/0174196 | A1 | 6/2015 | Gourdie et al. | |
| 2016/0287663 | A1 | 10/2016 | Gourdie et al. | |

FOREIGN PATENT DOCUMENTS

| JP | 2007-161688 A | 6/2007 |
| JP | 2009-504663 A | 2/2009 |
| JP | 2015-515282 A | 5/2015 |
| JP | 2017-14164 A | 1/2017 |
| JP | 6279801 B1 | 2/2018 |
| RU | 2 609 813 C1 | 2/2017 |

OTHER PUBLICATIONS

Li et al (Amino Acids, 2018; 50:29-38, published Sep. 20, 2017) (Year: 2017).*

(Continued)

*Primary Examiner* — Rayna Rodriguez
(74) *Attorney, Agent, or Firm* — Oblon, McClelland, Maier & Neustadt, L.L.P.

(57) ABSTRACT

Compositions containing at least four kinds of amino acids selected from the group consisting of serine, aspartic acid, glutamic acid, glycine, alanine and proline as active ingredients are useful for improving joint function and skin function and have high safety and permit continued ingestion or administration.

16 Claims, 8 Drawing Sheets

Specification includes a Sequence Listing.

*p<0.05, **p<0.01,
****p<0.001, unpaired t-test

(56) References Cited

OTHER PUBLICATIONS

All Star HealthSM (https://www.allstarhealth.com/de_p_ref/12161/pla12161/Now_Amino_Complete.htm? utm_source=google&utm_medium=GPS&utm_campaign=12161&gclid=CjwKCAjw9MuCBhBUEiwAbDZ-7hLMGDRRQA9sjCq9SptFMqQeNlrBA4KZLM5RwpWD8ir31WoVFSgoshoCbGUQAvD_BwE, with an available for sale date Aug. 23, 2014) (Year: 2014).*

Vieira, C. P. et al., "Glycine improves the remodeling process of tenocytes in vitro", Cell Biology International, 42, 7, 2018, pp. 804-814.

Vieira, C. P. et a., "Glycine Improves Biochemical and Biomechanical Properties Following Inflammation of the Achilles Tendon", The Anatomical Record 298, (Hoboken), 2015, pp. 538-545.

Notice of Reasons for Refusal dated Feb. 21, 2023 in Japanese Patent Application No. 2019-136362 (with English machine translation), citing documents 15-18 and 24 therein, 14 pages.

Yoo-Sin Park, et al., "Intra-articular injection of a nutritive mixture solution protects articular cartilage from osteoarthritic progression induced by anterior cruciate ligament transection in mature rabbits: a randomized controlled trial," Arthritis Research & Therapy. vol. 9. No. 1. R8, 2007. 9 pages.

* cited by examiner

*p<0.05, **p<0.01,
****p<0.001, unpaired t-test

*p<0.05, p<0.01, *p<0.005;

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
tcaagatggt ggccgttact        20

<210> SEQ ID NO 2
<211> LENGTH: 19
<212> TYPE: DNA
<213> ORGANISM: Artificial Sequence
<220> FEATURE:
<223> OTHER INFORMATION: synthetic primer

<400> SEQUENCE: 2
catcttgagg tcacggatg         19

<210> SEQ ID NO 3
<211> LENGTH: 20
<212> TYPE: DNA
<213> ORGANISM: Artificial Sequence
<220> FEATURE:
<223> OTHER INFORMATION: synthetic primer

<400> SEQUENCE: 3
aaatcggcaa ccctggtaga        20

<210> SEQ ID NO 4

```
<211> LENGTH: 20
<212> TYPE: DNA
<213> ORGANISM: Artificial Sequence
<220> FEATURE:
<223> OTHER INFORMATION: synthetic primer

<400> SEQUENCE: 4 ttctcccctta ggccctttgg                                               20

<210> SEQ ID NO 5
<211> LENGTH: 20
<212> TYPE: DNA
<213> ORGANISM: Artificial Sequence
<220> FEATURE:
<223> OTHER INFORMATION: synthetic primer

<400> SEQUENCE: 5
cctaagcacc ccaaaacacc                                                20

<210> SEQ ID NO 6
<211> LENGTH: 20
<212> TYPE: DNA
<213> ORGANISM: Artificial Sequence
<220> FEATURE:
<223> OTHER INFORMATION: synthetic primer

<400> SEQUENCE: 6
gggaagttct ggccaaaagg                                                20

<210> SEQ ID NO 7
<211> LENGTH: 20
<212> TYPE: DNA
<213> ORGANISM: Artificial Sequence
<220> FEATURE:
<223> OTHER INFORMATION: synthetic primer

<400> SEQUENCE: 7
caagttcaac ggcacagtca                                                20

<210> SEQ ID NO 8
<211> LENGTH: 20
<212> TYPE: DNA
<213> ORGANISM: Artificial Sequence
<220> FEATURE:
<223> OTHER INFORMATION: synthetic primer

<400> SEQUENCE: 8
ccccatttga tgttagcggg                                                20

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
tgcaactcgg acctggttat                                                20

<210> SEQ ID NO 10
<211> LENGTH: 20
<212> TYPE: DNA
<213> ORGANISM: Artificial Sequence
<220> FEATURE:
<223> OTHER INFORMATION: synthetic primer

<400> SEQUENCE: 10
```

```
gcgtcgaatc ctttgagcat                                               20

<210> SEQ ID NO 11
<211> LENGTH: 20
<212> TYPE: DNA
<213> ORGANISM: Artificial Sequence
<220> FEATURE:
<223> OTHER INFORMATION: synthetic primer

<400> SEQUENCE: 11
cttcatcatt caggcctgcc                                               20

<210> SEQ ID NO 12
<211> LENGTH: 20
<212> TYPE: DNA
<213> ORGANISM: Artificial Sequence
<220> FEATURE:
<223> OTHER INFORMATION: synthetic primer

<400> SEQUENCE: 12
cacgagtgag gatgtgcatg                                               20
```

COMPOSITION FOR IMPROVING JOINT FUNCTION

CROSS REFERENCES TO RELATED APPLICATIONS

This application claims priority to Japanese Patent Application No. JP2018-139806, filed on Jul. 25, 2018, which is incorporated herein by reference in its entirety.

BACKGROUND OF THE INVENTION

Field of the Invention

The present invention relates to compositions for improving joint function and a composition for improving skin condition, each containing particular amino acids.

Discussion of the Background

There have been many reports on the incidence of injuries of joints in athletes, such as injuries and rupture of tendons, muscle strain, cartilage injury, injuries and rupture of ligaments, and long-term withdrawal from the competition and poor performance due to injury, recurrence of injury and the like have been serious problems among athletes. For athletes, therefore, it is important to have a body that does not get injured and recovers in a short term for rapid return to competition even when the body is injured. Joint defects such as age-related joint failure and patellar tendonitis during the growth phase occur frequently from children to middle age and old people. Furthermore, in racehorses and the like, 1200 racehorses develop tendonitis every year, and the horses with severe symptoms are problematically forced to retire without sufficiently showing the expected performance.

Amino acids and peptides have been regularly used as medicaments, supplements or the like by the general public and athletes, and various physiological actions have been reported. For example, RU 2609813, which is incorporated herein by reference in its entirety, describes that amino jams containing hydrolyzed collagen, branched chain amino acid (BCAA), vitamin C, and the like are beneficial for improving skin condition, preventing damage to joints, tendons, ligaments, cartilage and other connective tissues, and for rehabilitation. JP-A-2015-515282, which is incorporated herein by reference in its entirety, also describes that an isolated peptide with an amino acid length of less than about 50 has an effect of promoting tissue recovery, anti-fibrotic property, anti-scarring property, anti-inflammatory property and/or regeneration.

SUMMARY OF THE INVENTION

Accordingly, it is one object of the present invention to provide composition capable of improving the function of a joint part such as a tendon and ligament, and improving skin condition.

It is another object of the present invention to provide an amino acid composition capable of supporting and creating an injury-free body by strengthening joints and safe for long-term ingestion.

It is another object of the present invention to provide novel methods for improving joint function.

It is another object of the present invention to provide novel methods for improving skin condition.

These and other objects, which will become apparent during the following detailed description, have been achieved by the inventors' discovery that many amino acids decrease in tendons at the time of tendonitis and surprisingly found that mere ingestion of particular amino acids can accelerate recovery of tendonitis and improve joint function and strength of the muscles connected to the joint, and can improve skin condition with reduced collagen, which resulted in the completion of the present invention.

Accordingly, the present invention provides the following.

(1) A composition for improving joint function comprising at least four kinds of amino acids selected from the group consisting of serine, aspartic acid, glutamic acid, glycine, alanine and proline as active ingredients.

(2) The composition of (1) wherein the improvement of joint function is improvement of joint disorder or prevention of joint disorder.

(3) The composition of (1) or (2) wherein the joint disorder is at least one selected from the group consisting of tendonitis, patellar tendonitis, muscle strain, cartilage injury, tendon rupture, ligament injury, ligament rupture, lacertus injury, bone fracture, cartilage wear and loss of muscle strength caused thereby.

(3-1) The composition of (1) or (2) wherein the joint disorder is at least one selected from the group consisting of tendonitis, patellar tendonitis, osteoarthritis, medial meniscus injury, osteochondritis dissecans, muscle strain, cartilage injury, tendon rupture, ligament injury, ligament rupture, lacertus injury, bone fracture, cartilage wear and loss of muscle strength caused thereby.

(4) The composition of (1) wherein the improvement of joint function is joint strengthening.

(5) The composition of any of (1) to (4) wherein the serine, aspartic acid, glutamic acid, glycine, alanine and proline are respectively contained at 0 to 30 wt %, 0 to 30 wt %, 0 to 20 wt %, 0 to 35 wt %, 0 to 30 wt % and 0 to 35 wt % relative to the total weight of serine, aspartic acid, glutamic acid, glycine, alanine and proline.

(6) The composition of any of (1) to (5) which is in a unit package form per serving for an adult comprising 10 mg to 50 g in total of the aforementioned amino acids as active ingredients for single ingestion.

(7) The composition of any of (1) to (6) which is a pharmaceutical product.

(8) The composition of any of (1) to (6) which is a food.

(9) A composition for improving skin condition comprising at least four kinds of amino acids selected from the group consisting of serine, aspartic acid, glutamic acid, glycine, alanine and proline as active ingredients.

(10) A method for improving joint function, comprising administering an effective amount of at least four kinds of amino acids selected from the group consisting of serine, aspartic acid, glutamic acid, glycine, alanine and proline as active ingredients to a subject in need thereof.

(11) The method according to (10), wherein the improvement of joint function is improvement of joint disorder or prevention of joint disorder.

(12) The method according to (11), wherein said joint disorder is at least one selected from the group consisting of tendonitis, patellar tendonitis, osteoarthritis, medial meniscus injury, osteochondritis dissecans, muscle strain, cartilage injury, tendon rupture, ligament injury, ligament rupture, lacertus injury, bone fracture, cartilage wear and loss of muscle strength caused thereby.

(13) The method according to (10), wherein the improvement of joint function is joint strengthening.

(14) The method according to (10), comprising administering said serine, aspartic acid, glutamic acid, glycine, alanine and proline respectively in an amount of 0 to 30 wt %, 0 to 30 wt %, 0 to 20 wt %, 0 to 35 wt %, 0 to 30 wt % and 0 to 35 wt %, relative to the total weight of serine, aspartic acid, glutamic acid, glycine, alanine and proline.

(15) The method according to (10), comprising administering said serine, aspartic acid, glutamic acid, glycine, alanine and proline in a unit package form per serving for an adult comprising 10 mg to 50 g in total of the said amino acids as active ingredients for single ingestion.

(16) A method for improving a skin condition, comprising administering an effective amount of at least four kinds of amino acids selected from the group consisting of serine, aspartic acid, glutamic acid, glycine, alanine and proline as active ingredients to a subject in need thereof.

(17) The method according to (16), comprising administering said serine, aspartic acid, glutamic acid, glycine, alanine and proline respectively in an amount of 0 to 30 wt %, 0 to 30 wt %, 0 to 20 wt %, 0 to 35 wt %, 0 to 30 wt % and 0 to 35 wt %, relative to the total weight of serine, aspartic acid, glutamic acid, glycine, alanine and proline.

Effect of the Invention

The amino acid composition provided by the present invention can accelerate recovery of joint wounds and suppress muscle weakness due to joint wounds.

The amino acid composition provided by the present invention can suppress and improve inflammation and disorder of joints, functional decrease, muscle weakness associated with joint inflammation and the like.

The amino acid composition provided by the present invention can improve skin condition.

The active ingredient in the present invention is amino acid, and therefore, it can be easily ingested safely for a long term.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
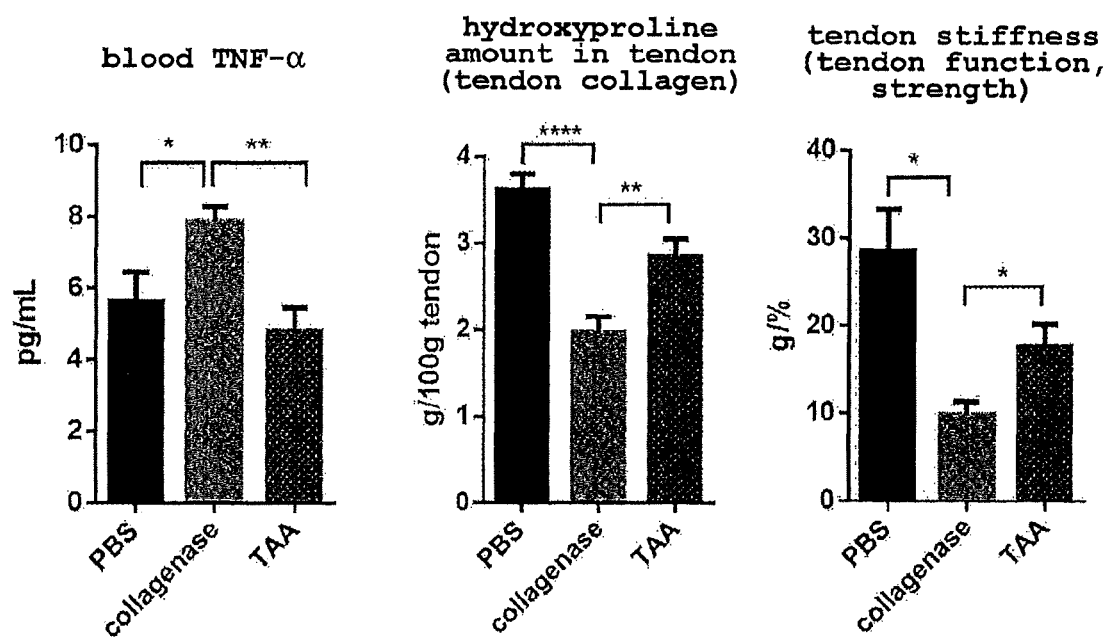
FIG. 1: A tendonitis rat was produced by injecting collagenase (4.5 mg/ml/leg) to Achilles tendon. PBS was similarly administered to the control group. The tendon function effect (stiffness), blood TNF-α concentration, and hydroxyproline amount (per 100 g tendon) in the tendon on day 14 after the onset of tendonitis are shown. PBS is a normal tendon group, collagenase is a tendonitis group, and TAA is a group in which TAA was mixed with a feed and the mixture was given to a tendonitis model rat.

The composition for improving joint function of the present invention contains at least four kinds of amino acids selected from the group consisting of (1) serine, (2) aspartic acid, (3) glutamic acid, (4) glycine, (5) alanine and (6) proline (hereinafter sometimes to be abbreviated as Ser, Asp, Glu, Gly, Ala and Pro, respectively) as active ingredients. As the composition for improving joint function of the present invention, a composition containing at least five kinds of amino acids selected from the group consisting of (1) to (6) as active ingredients is preferable, and a composition containing six kinds of amino acids is more preferable.

In the present specification, the "joint" means a movable part accompanying collagen metabolism, namely, tendon, ligament, cartilage, bone or lacertus.

The part includes the knee, elbow, shoulder, waist, wrist, ankle, neck, fingers, toes, back, hip joint, heel and muscle, and also includes superficial digital flexor tendon of the forelimb and the like of horse, and the like.

The "joint function improvement" means improvement, treatment, promotion of recovery of the disease state and symptoms related to the joint function, prevention of progression (exacerbation) of the disease state and symptoms, conditioning and prophylaxis. Examples of the disease state or symptom include joint disorder, pain, rigidity, low range of motion, wear, dissociation, detachment, foreign body sensation and the like.

Examples of the "joint disorder" include disease states or symptoms of inflammation of tendon and ligament, patellar tendonitis, osteoarthritis, medial meniscus injury, osteochondritis dissecans, rupture of tendon and ligament, muscle strain, cartilage injury, cartilage wear, ligament injury, lacertus injury, bone fracture, synovial inflammation, tendon and ligament weakness, joint inflammation, joint weakness, collagen decrease, tendovaginitis, discomfort of bending and stretching, difficulty in moving and the like, and the symptoms of loss of muscle strength, pain, inflammation caused by the aforementioned disease state or symptoms. Among these, the composition of the present invention is preferably used for tendonitis, patellar tendonitis, osteoarthritis, medial meniscus injury, osteochondritis dissecans, muscle strain, cartilage injury, tendon rupture, ligament injury, ligament rupture, lacertus injury, bone fracture, cartilage wear, joint inflammation, joint weakness, collagen decrease and loss of muscle strength caused thereby, and more preferably used for tendonitis, patellar tendonitis, osteoarthritis, muscle strain, cartilage injury, tendon rupture, ligament injury, ligament rupture, lacertus injury, bone fracture, cartilage wear and loss of muscle strength caused thereby.

Examples of the cause of joint disorder include damage of muscle tissues such as tendon, ligament, cartilage due to injury or sickness, collagen decrease, inflammation, pain, aging, rapid growth of bone, excessive loading (over use) in sports and repetitive works and the like, excessive stretching (elongation) and the like.

The "joint function improvement" also includes prophylaxis to prevent development of the disease state and symptoms related to joint function. The prophylaxis includes direct prevention which means preventing the onset of the disease state or symptom related to the joint function in a subject having or possibly having a risk of developing the disease state or symptom, and indirect prevention which means preventing the onset by strengthening the joint irrespective of the presence or absence of the risk.

The "joint strengthening" refers to strengthening and improvement of the function of the joint part. Particularly, it can support making of an injury-free body by strengthening the joints.

A composition for improving skin condition containing at least four kinds of amino acids selected from the group consisting of (1) serine, (2) aspartic acid, (3) glutamic acid, (4) glycine, (5) alanine and (6) proline as active ingredients is also encompassed in the present invention (hereinafter the composition for improving joint function and the composition for improving skin condition are sometimes to be generically referred to as the composition of the present invention). Among others, a composition for improving skin condition containing at least five kinds of amino acids selected from the group consisting of (1) to (6) as active ingredients is preferable, and a composition for improving skin condition containing six kinds of amino acids is more preferable.

The composition for improving skin condition of the present invention is used for improving skin condition associated with a decrease in collagen and recovering the decrease in collagen amount in the skin.

The skin condition can be improved by, for example, reducing wrinkles, regenerating the skin, improving skin elasticity, wound healing, improving acne and the like. A decrease in collagen amount is caused by aging, disease, injury and the like.

In the composition of the present invention, the combination of serine, aspartic acid, glutamic acid, glycine, alanine and proline is not limited as long as at least four kinds of amino acids selected therefrom are contained as the active ingredients. A combination of four kinds of amino acids of serine, glutamic acid, glycine, proline can be mentioned since the combination is superior in the anti-inflammatory effect, collagen synthesis promotion, tendon strengthening, recovery of muscle strength. A combination of five kinds of amino acids of serine, glutamic acid, glycine, proline, alanine is preferable, and a combination of six kinds of amino acids of serine, glutamic acid, glycine, proline, alanine, aspartic acid is more preferable.

While the serine, aspartic acid, glutamic acid, alanine and proline contained in the composition of the present invention may be any of L-form, D-form and DL-form, the L-form is preferable.

The amino acid in the present invention may be produced by any production method such as a protein hydrolysis method, a chemical synthesis method, an enzyme method, a fermentation method and the like, and commercially available products can also be used.

The amino acid in the present invention can also be obtained by enzymatically hydrolyzing a natural protein having an amino acid sequence.

The amino acid in the present invention can be used not only in a free form but also a salt form. The terms serine, aspartic acid, glutamic acid, glycine, alanine and proline in the present specification are each a concept encompassing even a salt. The salt form is not particularly limited as long as it is a pharmacologically acceptable salt, acid addition salt, salt with base and the like can be mentioned.

Concrete examples of the salt include salts with inorganic bases, salts with organic bases, salts with inorganic acids, salts with organic acids, salts with amino acid and the like.

Examples of the salts with inorganic bases include salts with alkali metals such as lithium, sodium, potassium and the like, salts with alkaline earth metals such as magnesium, calcium and the like, ammonium salt and the like.

Examples of the salts with organic bases include salts with an alkanolamine such as monoethanolamine, diethanolamine, triethanolamine and the like, salts with a heterocyclic amine such as morpholine, piperidine and the like, and the like.

Examples of the salts with inorganic acids include salts with a hydrohalic acid (hydrochloric acid, hydrobromic acid, hydroiodic acid etc.), sulfuric acid, nitric acid, phosphoric acid and the like.

Examples of the salts with organic acids include salts with a monocarboxylic acid such as formic acid, acetic acid, propanoic acid and the like; salts with a saturated dicarboxylic acid such as oxalic acid, malonic acid, malic acid, succinic acid and the like; salts with an unsaturated dicarboxylic acid such as maleic acid, fumaric acid and the like; salts with a tricarboxylic acid such as citric acid and the like; salts with a keto acid such as α-ketoglutaric acid and the like.

Examples of the salts with amino acid include salts with an aliphatic amino acid such as glycine, alanine and the like; salts with an aromatic amino acid such as tyrosine and the like; salts with a basic amino acid such as arginine and the like; salts with an acidic amino acid such as aspartic acid, glutamic acid and the like; salts with an amino acid forming lactam such as pyroglutamic acid and the like; and the like.

The above-mentioned salts may each be a hydrate (hydrate salt), and examples of such hydrate include 1 hydrate to 6 hydrates and the like.

In the present invention, one kind of amino acid in a free form or the above-mentioned salt form may be used singly, or two or more kinds thereof may be used in combination.

In the present invention, from the viewpoint of eating experience and easy availability, serine is preferably in a free form is preferable, aspartic acid is preferably in a free form or a sodium salt or the like, glutamic acid is preferably in a free form or a sodium salt or the like, glycine is preferably in a free form, alanine is preferably in a free form, and proline is preferably in a free form.

In the present invention, the weight (%) of each amino acid in terms of an L form and free form is generally (1) serine 0 to 30 wt %, (2) aspartic acid 0 to 30 wt %, (3) glutamic acid 0 to 20 wt %, (4) glycine 0 to 35 wt %, (5) alanine 0 to 30 wt % and (6) proline 0 to 35 wt %, preferably (1) 10 to 30 wt %, (2) 10 to 30 wt %, (3) 10 to 20 wt %, (4) 10 to 35 wt %, (5) 10 to 30 wt % and (6) 10 to 35 wt %, more preferably (1) 10 to 20 wt %, (2) 10 to 20 wt %, (3) 10 to 20 wt %, (4) 10 to 30 wt %, (5) 10 to 25 wt % and (6) 10 to 30 wt %, further preferably (1) 5 to 20 wt %, (2) 10 to 17 wt %, (3) 10 to 18 wt %, (4) 14 to 30 wt %, (5) 12 to 25 wt % and (6) 14 to 25 wt %. The above-mentioned weight (%) of each amino acid is weight (%) relative to the total weight of serine, aspartic acid, glutamic acid, glycine, alanine and proline.

The amino acid in the present invention means a free amino acid, and does not include constituent amino acids in protein or peptide. In the present specification, the content of each amino acid is the content of amino acid in an L form. When the amino acid is contained in a salt form, the content is shown by conversion of the salt to a free form. The amino acid composition of the present invention may contain an amino acid in a D form. When an amino acid in a DL form is contained, the content can be converted based on the content of amino acid in an L form.

In the composition of the present invention, the weight ratio of serine, aspartic acid, glutamic acid, glycine, alanine and proline as the active ingredients is generally 1:0 to 5:0 to 5:1 to 5:1 to 5:1 to 5, preferably 1:0 to 4:0 to 4:1 to 4:1 to 4:1 to 4, more preferably 1:0 to 2:0 to 3:1 to 4:1 to 4:1 to 3.

In the composition of the present invention, the another weight ratio of serine, aspartic acid, glutamic acid, glycine, alanine and proline as the active ingredients is generally 0 to 1:0 to 5:0 to 5:0 to 5:0 to 5, preferably 1:0 to 4:1 to 4:1 to 4:0 to 4:1 to 4, more preferably 1:1 to 2:1 to 3:1 to 4:1 to 4:1 to 3.

While the dose (ingestion amount for adult) of the composition of the present invention may vary depending on the age, sex, body weight, target disease, symptom, and dosage form, the daily dose of amino acids (1) to (6) in total is generally 10 mg to 50 g, preferably 100 mg to 40 g, more preferably 100 mg to 30 g, for an adult (e.g., body weight 60 kg), which is administered or ingested in one to several portions per day.

The dose (ingestion amount) of (1) is generally 0 g to 20 g, preferably 0 g to 5 g, more preferably 15 mg to 5 g, for an adult per day.

The dose (ingestion amount) of (2) is generally 0 g to 20 g, preferably 0 g to 5 g, more preferably 16.5 mg to 5 g, for an adult per day.

The dose (ingestion amount) of (3) is generally 0 g to 20 g, preferably 0 g to 5 g, more preferably 15 mg to 5 g, for an adult per day.

The dose (ingestion amount) of (4) is generally 0 g to 20 g, preferably 0 g to 5 g, more preferably 16.5 mg to 5 g, for an adult per day.

The dose (ingestion amount) of (5) is generally 0 g to 20 g, preferably 0 g to 5 g, more preferably 17 mg to 5 g, for an adult per day.

The dose (ingestion amount) of (6) is generally 0 g to 20 g, preferably 0 g to 5 g, more preferably 20 mg to 5 g, for an adult per day.

The above-mentioned dose for an adult per day can be changed as appropriate in consideration of the sex, age, condition of the body such as disease and the like.

The above-mentioned dose of the composition of the present invention can be administered all at once or in several portions. The dosing period is not particularly limited, and long-term administration is possible since the active ingredient is amino acid.

For example, patellar tendonitis developed by decreased thigh muscle extensibility due to over use (mechanical stress) and growth of bone can be divided into the following phases:

phase 1: pain is noticed after sport activities but no hindrance to sport activities phase 2: pain is noticed during and after sport activities but no hindrance to sport activities phase 3: pain is constantly noticed and hinders sport activities phase 4: surgery and postoperative rehabilitation are necessary.

The composition of the present invention can be administered at any phase.

These also apply to the cases of disorder, functional decrease and rupture of all joint parts. That is, administration of the composition of the present invention to tendonitis in phases 1 and 2 can improve the condition of tendon and bring the same to the normal state and further prevent progression to phase 3. In phase 4, administration during rehabilitation can promote recovery. In the case of tendon or ligament rupture, which means phase 4 alone, postoperative administration or administration during preservation therapy can promote recovery. In addition, recovery of tendonitis can be promoted by administering the composition of the present invention even in the case of chronic tendonitis in phase 3 caused by over use after once healing.

The composition of the present invention recovers the collagen amount, which in turn promotes collagen synthesis not only in the movable parts but also epidermis, and can normalize skin condition, recover skin collagen amount that decreased due to aging and the like and improve skin condition.

The composition of the present invention can contain, besides the amino acids in the present invention, other nutrition components such as carbohydrates, lipids, proteins, amino acids other than the amino acids of the above-mentioned (1) to (6), vitamins, minerals and the like.

For example, when an amino acid other than serine, aspartic acid, glutamic acid, glycine, alanine and proline is contained in the composition, its proportion in terms of a free form is not more than 10 wt %, preferably not more than 5 wt %, to the total weight of the amino acids in the composition. The composition of the present invention is further preferably substantially free of and particularly preferably free of, amino acid other than serine, aspartic acid, glutamic acid, glycine, alanine and proline. Being substantially free means containing not more than 0.2 wt %, preferably not more than 0.1 wt %, more preferably not more than 0.05 wt %, based on the total weight of the composition.

The composition of the present invention containing the amino acids in the present invention, other nutrition components, pharmaceutically acceptable additives and the like can be formulated into various forms such as liquid form (e.g., solution, suspension, emulsion and the like); semi-solid form (e.g., gel, cream and the like); solid form (e.g., powder, granule, tablet, capsule and the like) and the like by a formulating means well known in the field of preparations, for example, the methods described in the Japanese Pharmacopoeia preparation, seventeenth Edition, General Rules [3] preparation, each article, which is incorporated herein by reference in its entirety, and the like.

The above-mentioned pharmaceutically acceptable additive can be appropriately selected according to the dosage form of the composition of the present invention. For example, an excipient, binder, disintegrant, lubricant, coating agent, base, solvent, solubilizing agents, solubilizer, emulsifier, dispersing agent, suspending agent, stabilizer, thickener, soothing agent, isotonicity agent, pH adjuster, antioxidant, antiseptic, preservative, corrigent, sweetening agent, flavor, colorant and the like can be mentioned.

Specifically, examples of the excipient include magnesium carbonate, saccharides (glucose, lactose, cornstarch etc.), sugar alcohol (sorbitol, mannitol etc.) and the like.

Examples of the binder include gelatin, pregelatinized starch, partly pregelatinized starch, cellulose and a derivative thereof (crystalline cellulose, hydroxypropylcellulose etc.) and the like.

Examples of the disintegrant include crospovidone, povidone, crystalline cellulose and the like.

Examples of the lubricant include talc, magnesium stearate and the like.

Examples of the coating agent include methacrylic acid-methyl methacrylate copolymer, methacrylic acid.ethyl acrylate copolymer, methyl methacrylate.butyl methacrylate.methacrylic acid dimethylaminoethyl copolymer, ethyl acrylate.methyl methacrylate.methacrylic acid trimethylammonium chloride ethyl copolymer and the like.

Examples of the base include animal and plant fats and oils (olive oil, cacao butter, beef tallow, sesame oil, hydrogenated oil, castor oil etc.), wax (Carnauba wax, beeswax etc.), polyethylene glycol and the like.

Examples of the solvent include purified water, water for injection, a monovalent alcohol (ethanol etc.), a polyhydric alcohol (glycerol etc.) and the like.

Examples of the solubilizing agents include propylene glycol, medium-chain triglycerides and the like.

Examples of the solubilizer, emulsifier, dispersing agent and suspending agent include surfactants such as sorbitan fatty acid ester, glycerol fatty acid ester, polyoxyethylene sorbitan fatty acid ester (polysorbate20, polysorbate80 etc.), polyoxyethylene hydrogenated castor oil, sucrose fatty acid ester and the like, and the like.

Examples of the stabilizer include adipic acid, β-cyclodextrin, ethylenediamine, sodium edetate and the like.

Examples of the thickener include water-soluble polymers (sodium polyacrylate, carboxyvinyl polymer etc.), polysaccharides (sodium alginate, xanthan gum, tragacanth etc.) and the like.

Examples of the soothing agent include ethyl aminobenzoate, chlorobutanol, propylene glycol, benzyl alcohol and the like.

Examples of the isotonicity agent include potassium chloride, sodium chloride, sorbitol, saline and the like.

Examples of the pH adjuster include hydrochloric acid, sulfuric acid, acetic acid, citric acid, lactic acid, sodium hydroxide, potassium hydroxide and the like.

Examples of the antioxidant include dibutylhydroxytoluene (BHT), butylhydroxyanisole (BHA), dl-α-tocopherol, erythorbic acid and the like.

Examples of the antiseptic and preservative include paraben (methylparaben etc.), benzyl alcohol, sodium dehydroacetate, sorbic acid and the like.

Examples of the corrigent include ascorbic acid, erythritol, L-sodium glutamate and the like.

Examples of the sweetening agent include aspartame, licorice extract, saccharin and the like.

Examples of the flavor include l-menthol, d-camphor, vanillin and the like.

Examples of the colorant include tar pigment (Food Color Red No. 2, Food Color Blue No. 1, Food Color yellow No. 4 etc.), inorganic pigment (red ferric oxide, yellow iron oxide, black iron oxide etc.), natural dye (turmeric extract, β-carotene, sodium copper chlorophyllin etc.) and the like.

In the present invention, one or more kinds of the above-mentioned additives can be used.

From the aspect of function, the total content of the amino acids in the composition of the present invention is generally 10 wt % to 100 wt %, preferably 50 wt % to 100 wt %, more preferably 80 wt % to 100 wt %, to the total amount of the composition.

The composition of the present invention may be in the form of a package of a unit ingestion amount for one time or one meal, "unit package form". In such an embodiment, the amount to be ingested once or per meal is determined in advance and packaged. The container or package used for the unit package form can be appropriately selected according to the form and the like of the composition of the present invention. Examples thereof include a paper container or sack, plastic container or sack, pouch, aluminum can, steel can, glass bottle, plastic bottle, PTP (press through pack) package sheet and the like. Examples thereof include a form of a package of an amount to be ingested at one time using a container such as a pack, bag, bottle, box in the case of drinks, jelly, yogurt, gum, cookie and the like, and a form of an individual package of an amount to be ingested at one time using a pack, bag and the like in case of the granule, powder, slurry and the like. Particularly, when the composition is a health food, food with functional claims, food with nutrient function claims, food for specified health uses and the like, for example, a form wherein the composition of the present invention is packed in a unit amount to be ingested once or per meal, a form wherein the composition of the present invention is suspended or dissolved to give a drink or a jelly, which is packaged in a pack etc. for a single consumption or ingestion and the like can be mentioned.

The above-mentioned ingestion amount for one time or one meal can contain 10 mg to 50 g, preferably 100 mg to 30 g, more preferably 100 mg to 20 g, in total of four to six amino acids from serine, aspartic acid, glutamic acid, glycine, alanine and proline. In this way, ingestion of one time or one meal unit ingestion amount enables convenient ingestion of the necessary amount of amino acid.

Another embodiment of the present invention is a kit containing a measuring container, and a composition containing four to six amino acids from serine, aspartic acid, glutamic acid, glycine, alanine and proline as active ingredients.

The measuring container is not particularly limited as long as it is a container for measuring the amount of single ingestion of the above-mentioned amino acids and, for example, a measuring cup, a measuring spoon and the like can be mentioned. The amount of single ingestion is the same as the above-mentioned single ingestion or serving amount. The amount that can be measured by a measuring container can be determined according to the container such as a level amount, a heaping amount and the like. The measuring container may have a scale showing the amount of single use and the like.

Still another embodiment is a high volume packaging form in which a composition containing four to six amino acids from serine, aspartic acid, glutamic acid, glycine, alanine and proline as active ingredients is packaged and the packaging form itself or instruction sheet indicates that the amount of single ingestion is the above-mentioned single ingestion or serving amount.

The form of the composition of the present invention may be liquid (drinks and the like), jelly (jelly, gel, jelly drinks and the like), milky (milk, milk beverage, yogurt and the like), solid (gum, powdered, granular, sheet, capsule, tablet, candy bar, cookies and the like), and the like.

The composition of the present invention can be applied to mammals (e.g., human, monkey, mouse, rat, guinea pig, hamster, rabbit, cat, dog, bovine, horse, donkey, swine, sheep etc.), birds (e.g., duck, chicken, goose, turkey etc.) and the like.

When the composition of the present invention is applied to an application target animal other than human (hereinafter to be also simply referred to as "target animal"), the ingestion amount or dose of the composition of the present invention can be appropriately set according to the kind, sex, body weight and the like of the target animal.

The composition of the present invention can be provided as it is or as a pharmaceutical product further containing the above-mentioned pharmaceutically acceptable additives (hereinafter to be also referred to as "the pharmaceutical product of the present invention" in the present specification).

The pharmaceutical product of the present invention can have a dosage form of oral preparation such as tablet, coating tablet, chewable tablet, pill, (micro)capsule, granule, fine granule, powder, elixir, lemonade, syrup, suspension, emulsion, oral jelly and the like, injection preparation such as a solution, suspension, emulsion and the like, solid injection to be used by dissolving or suspending when in use, injectable preparation such as transfusion, sustainable injection and the like, tube feeding liquid and the like.

The pharmaceutical product of the present invention can be administered to athletes, elderly people, middle-aged people and the like, children in a growth stage, who have decreased joint function or joint disorder, and athletes, elderly people, middle-aged people and the like, children in a growth stage, who may develop the afore-mentioned disorder. It may also be administered to animals whose joints are loaded such as racehorses and the like.

The pharmaceutical product of the present invention can be administered to a wide range of age groups, from elderly people and middle-aged people to children, showing decreased skin condition or who may show decreased skin condition due to aging, disease, wounds and the like.

The pharmaceutical product of the present invention can be administered to a wide range of age groups, from elderly people and middle-aged people to children, having osteoarthritis or who may develop osteoarthritis.

The pharmaceutical product of the present invention is administered to the above-mentioned application subject such that the total amount of the amino acids in the present invention (total amount in terms of L form and free form) would be the above-mentioned ingestion amount per day.

Furthermore, the composition of the present invention can be ingested by adding it to various foods. The food to which the composition of the present invention is added is not particularly limited, and may be any as long as it is a food in the form generally served for meals and dessert. For example, the composition of the present invention is added to drinks (e.g., beverage etc.), and a suitable flavor is added when desired, whereby a drink can be provided.

More specifically, the composition of the present invention can be added to, for example, a beverage water such as fruit juice drinks, sport drinks and the like; milk product such as cow milk, yogurt and the like; a confectionery such as jelly, chocolate, candy, biscuit and the like, and the like.

The composition of the present invention is preferably added to the above-mentioned various foods in amounts to be ingested per day such that the total amount of the amino acids in the present invention (total amount in terms of L form and free form) would be the above-mentioned ingestion amount per day.

The composition of the present invention can be provided as it is or as a food by adding general food additives where necessary by a general food production technique (hereinafter to be also referred to as "food of the present invention" in the present specification).

The food of the present invention can be formulated into various forms such as liquid, suspension, milk, gel, cream, powder, granule, sheet, capsule, tablet and the like.

Furthermore, the food of the present invention can be provided in various forms of foods containing the composition of the present invention and various food starting materials and, where necessary, general food additives by a general food production technique. Examples thereof include a beverage water (fruit juice drinks, sport drinks, coffee drinks, tea drinks etc.), milk product (*lactobacillus* drinks, fermentation milk, butter, cheese, yogurt, processed milk, defatted milk etc.), meat product (ham, sausage, hamburger steak etc.), processed seafood paste product (fish cake, tube-shaped fish sausage, satsumaage etc.), egg product (Japanese-style rolled omelette, egg tofu etc.), confectionery (cookie, jelly, chewing gum, candy, snack confectionery, frozen dessert etc.), bread, noodles, pickles, dried fish, boiled fish, soup, seasoning and the like. It may also be bottled food, canned food or retort pouch food.

Examples of the above-mentioned food additive include agents for production (kansui, binding agent etc.), thickening stabilizer (xanthan gum, sodium carboxymethylcellulose etc.), gelation agent (gelatin, agar, carrageenan etc.), gum base (vinyl acetate resin, jelutong, chicle etc.), emulsifier (glycerol fatty acid ester, sucrose fatty acid ester, saponin, lecithin etc.), preservative (benzoic acid, sodium benzoate, sorbic acid, potassium sorbate, $\varepsilon$-polylysine etc.), antioxidant (ascorbic acid, erythorbic acid, catechin etc.), gloss agent (shellac, paraffin wax, beeswax etc.), fungicide (thiabendazole, fludioxonil etc.), leavening agent (sodium hydrogen carbonate, glucono $\delta$-lactone, alum etc.), sweetener (aspartame, acesulfame potassium, licorice extract etc.), bittering agent (caffeine, naringin, worm wood extract etc.), acidulant (citric acid, tartaric acid, lactic acid etc.), seasoning (L-sodium glutamate, disodium 5'-inosinate etc.), colorant (annatto dye, turmeric dye, gardenia dye etc.), flavor (synthetic flavor such as ethyl acetoacetate, anisaldehyde and the like, natural flavor such as orange, lavender and the like) and the like.

In the present invention, one or more kinds of the above-mentioned food additive can be used.

The food of the present invention can be preferably given to athletes, elderly people, middle-aged people and the like, children in a growth stage who have joint functional decrease or joint disorder, and athletes, elderly people, middle-aged people and the like, children in a growth stage who may develop the afore-mentioned disorder. As a result, the function of the joint parts such as tendon, ligament and the like of athletes, elderly people and the like can be improved, joint disorder and wound recovery can be improved, and performance of athletes and QOL of elderly people can be improved. Furthermore, it can be preferably taken by a wide range of target subjects for the purpose of improving decreased joint function, strengthening joints and creating a body that does not get injured easily. It may also be given to animals whose joints are loaded such as racehorses and the like.

The food of the present invention can be given to a wide range of age groups, from elderly people and middle-aged people to children, showing decreased skin condition or who may show decreased skin condition due to aging, disease, wound and the like.

The food of the present invention can be given to a wide range of age groups, from elderly people and middle-aged people to children, having osteoarthritis or possibly developing osteoarthritis.

Therefore, the food of the present invention can also be provided as food with health claims such as food for specified health uses, food with nutrient function claims, food with functional claims and the like for the maintenance or improvement of physical ability for performance, special purpose foods such as food for sick people, food for the elderly and the like, health supplement and the like for joint function improvement and joint strengthening or improvement of skin condition, particularly osteoarthritis.

The food of the present invention is preferably given to the above-mentioned application subject such that the total amount of the amino acids in the present invention (total amount in terms of L form and free form) would be the above-mentioned ingestion amount per day.

In the present specification, unless otherwise specified, % means wt %.

Other features of the invention will become apparent in the course of the following descriptions of exemplary embodiments which are given for illustration of the invention and are not intended to be limiting thereof.

EXAMPLES

Various measurement methods are as follows.

Measurement of Collagen Amount in Tendon

The collagen contained in Achilles tendon is insoluble collagen. Thus, tendon was hydrolyzed and the concentration of hydroxyproline and other amino acids was measured using an amino acid analyzer (HITACHI high-speed amino acid analyzer L-8900).

The amount of collagen in tendon is generally calculated by considering the amount of hydroxyproline as the amount of insoluble collagen. The higher the amount of hydroxyproline, the higher the amount of collagen.

Stiffness Measurement (Tendon Function Evaluation)

Achilles tendon on the left foot was immersed in PBS solution until stiffness was measured. Using a texture analyzer, stiffness (g/%) was calculated using the force (g) and strain (%) required for pulling the tendon by 5%. A higher stiffness value means that the tendon is strong.

TNF-α Measurement (Anti-Inflammation Evaluation)

Plasma component was separated by centrifuging the collected blood at 10000 rpm×5 min. The measurement was performed using the plasma and according to the protocol of rat TNF alpha ELISA kit (Thermo Fischer KRC3011). A higher TNF-α value shows stronger inflammation.

Maximum Gastrocnemius Muscle Strength Measurement

As the exercise load, the left leg of the animal was fixed to torque under anesthesia, and an NSC electrode (NIHON KOHDEN CORPORATION) was applied to gastrocnemius muscle. Isometric contraction of the ankle joint plantar flexor muscles was caused by applying electrical stimulation, during which stretchable contraction to perform 90 degree dorsiflexion exercise was applied 10 times using the torque. A rest period for 1 minute was allowed and the operation was performed for 10 sets. As to the maximum muscle strength, electric stimulation was applied before and after the exercise load and passive ankle joint dorsiflexion resistance torque was measured to reflect the force required for maximum elongation.

Gene Analysis in Tendon and Muscle

For gene analysis, the collected tendon and gastrocnemius connected thereto were homogenated using Tripure isolation reagent (Roche) (1 ml), and RNA was extracted according to the attached protocol. Using the extracted RNA and according to PrimeScrip RT reagent kit (TAKARA), cDNA was synthesized. Using the synthesized cDNA, qPCR was performed using the following primers, the expression level of each gene was normalized with the expression level of GAPDH and the relative value was calculated.

Col1a: collagen synthase

MMP-13: collagen degradation enzyme

GAPDH: house keeping gene (for normalization)

```
Col1a1a1 (F)
                              (SEQ ID NO: 1)
TCAAGATGGTGGCCGTTACT

Col1a1a1 (R)
                              (SEQ ID NO: 2)
CATCTTGAGGTCACGGATG

Col1a1a2 (F)
                              (SEQ ID NO: 3)
AAATCGGCAACCCTGGTAGA

Col1a1a2 (R)
                              (SEQ ID NO: 4)
TTCTCCCTTAGGCCCTTTGG

MMP-13 (F)
                              (SEQ ID NO: 5)
CCTAAGCACCCCAAAACACC

MMP-13 (R)
                              (SEQ ID NO: 6)
GGGAAGTTCTGGCCAAAAGG

GAPDH (F)
```

-continued

MMP-13 (F)
(SEQ ID NO: 5)
CCTAAGCACCCCAAAACACC

MMP-13 (R)
(SEQ ID NO: 6)
GGGAAGTTCTGGCCAAAAGG

GAPDH (F)
(SEQ ID NO: 7)
CAAGTTCAACGGCACAGTCA

GAPDH (R)
(SEQ ID NO: 8)
CCCCATTTGATGTTAGCGGG

IL-1β Measurement (Anti-Inflammation Evaluation)

Plasma component was separated by centrifuging the collected blood at 10000 rpm×5 min. The measurement was performed using the plasma and according to the protocol of rat IL-1β ELISA kit (abcam). A higher IL-1β value shows stronger inflammation.

CTX-II Measurement (Cartilage Collagen Degradation Evaluation)

Plasma component was separated by centrifuging the collected blood at 10000 rpm×5 min. The measurement was performed using the plasma and according to the protocol of rat CTX-II ELISA kit (CUSABIO). A higher CTX-II value shows stronger cartilage collagen degradation.

Gene Expression Analysis in Cartilage Tissue

The collected cartilage tissue was homogenated using Tripure isolation reagent (Roche) (1 ml), and RNA was extracted according to the attached protocol. Using the extracted RNA and according to PrimeScrip RT reagent kit (TAKARA), cDNA was synthesized. Using the synthesized cDNA, qPCR was performed using the following primers, the expression level of each gene was normalized with the expression level of GAPDH and the relative value was calculated.

A high expression level of each gene shows injury and decrease of cartilage.

MMP-13: collagen degradation enzyme

TIMP-1: osteoclast forming factor

Caspase3: chondrocyte apoptosis-related enzyme

MMP-13 (F)
(SEQ ID NO: 5)
CCTAAGCACCCCAAAACACC

MMP-13 (R)
(SEQ ID NO: 6)
GGGAAGTTCTGGCCAAAAGG

GAPDH (F)
(SEQ ID NO: 7)
CAAGTTCAACGGCACAGTCA

GAPDH (R)
(SEQ ID NO: 8)
CCCCATTTGATGTTAGCGGG

TIMP-1 (F)
(SEQ ID NO: 9)
TGCAACTCGGACCTGGTTAT

TIMP-1 (R)
(SEQ ID NO: 10)
GCGTCGAATCCTTTGAGCAT

Caspase3 (F)
(SEQ ID NO: 11)
CTTCATCATTCAGGCCTGCC

Caspase3 (R)
(SEQ ID NO: 12)
CACGAGTGAGGATGTGCATG

Example 1

Preparation of Tendonitis Model (1) 10-week-old male F344 rats (body weight 230 to 240 g) were anesthetized with isoflurane, the skin on the Achilles tendon of both legs was incised and the Achilles tendon was exposed. Thereto was injected collagenase (4.5 mg/ml/leg) and the skin was sutured to construct a tendonitis model.

(2) The same amount of phosphate buffered saline (PBS) was injected into the Achilles tendon instead of collagenase to give a normal tendon group. PBS used was produced by Takara Bio Inc.

(3) Immediately after putting back into the cage, a normal feed (16% casein-containing feed) was given to the normal tendon group and the tendonitis group, a mixed feed containing 2% (weight ratio) of amino acids at the proportion shown in Table 1 was given to the tendonitis+TAA group and all groups were bred for 2 weeks. The values of the amino acids in Table 1 are based on L form and free form. The constitution of the groups is shown in Table 2.

(4) After 2 weeks, blood, Achilles tendon, gastrocnemius were collected under isoflurane anesthesia, and anti-inflammation (TNF-α measurement), tendon function (stiffness measurement) and tendon collagen amount were evaluated.

TABLE 1

| | TAA |
|---|---|
| Ser | 15 |
| Asp | 16.5 |
| Glu | 15 |
| Gly | 16.5 |
| Ala | 17 |
| Pro | 20 |
| % | 100 |

TABLE 2

| group | feed | n |
|---|---|---|
| normal tendon group | PBS administration + normal feed | 8 |
| tendonitis group | collagenase administration + normal feed | 10 |
| tendonitis + TAA group | collagenase administration + normal feed + TAA | 10 |

As shown in FIG. 1, TAA significantly suppressed inflammation during tendonitis, and showed recovery of tendon hydroxyproline amount (collagen amount) and tendon stiffness (rigidity). In view of the recovery of collagen amount by TAA, TAA is expected to promote collagen synthesis in the parts where collagen metabolism is active, for example, skin and the like.

Example 2

Gastrocnemius Muscle Strength Evaluation in Tendonitis Model (1) 10-Week-old male F344 rats (body weight 230 to 240 g) were anesthetized with isoflurane, the skin on the Achilles tendon of both legs was incised and the Achilles tendon was exposed. Thereto was injected collagenase (4.5 mg/ml/leg) and the skin was sutured to construct a tendonitis model.

(2) The same amount of PBS was injected into the Achilles tendon instead of collagenase to give a normal tendon group.

(3) Immediately after putting back into the cage, a normal feed (16% casein-containing feed) was given to the normal tendon group and the tendonitis group, a mixed feed containing 2% of sample at the proportion shown in Table 1 was given to the tendonitis+TAA group and all groups were bred for 3 weeks.

(4) After 3 weeks, an electric stimulation exercise load (electric stimulation (90°×10 sets), eccentric exercise) was applied and muscle strength was measured. The constitution of the groups is shown in Table 3.

(5) After 1 week, blood, Achilles tendon, gastrocnemius were collected under isoflurane anesthesia, and muscle strength, aminogramme, anti-inflammation (blood TNF-α), and tendon, muscle inflammation marker (gene expression) were evaluated. The effect on the loss of muscle strength due to tendonitis was evaluated.

TABLE 3

| group | feed | n |
|---|---|---|
| normal tendon group | PBS administration + normal feed + EX (electric stimulation) | 8 |
| tendonitis group | collagenase administration + normal feed + EX (electric stimulation) | 10 |
| tendonitis + TAA group | collagenase administration + normal feed + TAA + EX (electric stimulation) | 11 |

Figure 2:
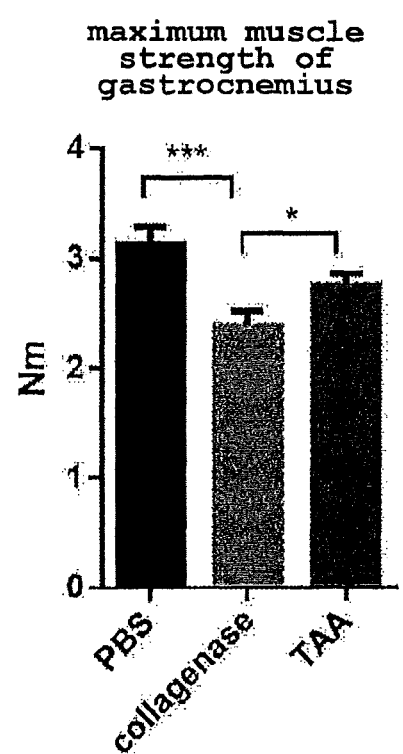
FIG. 2 shows the evaluation of the muscle strength of gastrocnemius on day 21 after the onset of tendonitis. PBS is a normal tendon group, collagenase is a tendonitis group, and TAA is a group in which TAA was mixed with a feed and the mixture was given to a tendonitis model rat. The vertical axis shows the strength of muscles (Nm).

The results are shown in FIG. 2. As shown in FIG. 2, TAA significantly recovered loss of muscle strength during tendonitis.

Ingestion of TAA exhibited a significant recovery effect on the loss of muscle strength during tendonitis.

Example 3

TAA1-6 Composition Evaluation in Tendonitis Model (1) 10-Week-old male F344 rats (body weight 230 to 240 g) were anesthetized with isoflurane, the skin on the Achilles tendon of both legs was incised and the Achilles tendon was exposed. Thereto was injected collagenase (4.5 mg/ml/leg) and the skin was sutured to construct a tendonitis model.

(2) Immediately after putting back into the cage, a normal feed (16% casein-containing feed) was given to the tendonitis group, a mixed feed containing 2% TAA1-6 was given to the TAA1-6 group, and all groups were bred for 2 weeks. The composition of TAA1-6 is shown in Table 4. The values of the amino acids in Table 4 are based on L form and free form. The constitution of the groups is shown in Table 5.

(3) After 2 weeks, blood, Achilles tendon, gastrocnemius were collected under isoflurane anesthesia, and anti-inflammation (TNF-α measurement) and gene (tendon, muscle) were evaluated.

TABLE 4

|  | TAA1 | TAA2 | TAA3 | TAA4 | TAA5 | TAA6 |
|---|---|---|---|---|---|---|
| Ser |  | 18 | 17.7 | 18 | 18.1 | 18.8 |
| Asp | 19.5 |  | 19.4 | 19.7 | 19.9 | 20.6 |
| Glu | 17.6 | 18 |  | 18 | 18.1 | 18.8 |
| Gly | 19.4 | 19.7 | 19.4 |  | 19.9 | 20.6 |
| Ala | 20 | 20.3 | 20 | 20.3 |  | 21.2 |
| Pro | 23.5 | 24 | 23.5 | 24 | 24 |  |
| total (%) | 100 | 100 | 100 | 100 | 100 | 100 |

TABLE 5

| group | feed | n |
|---|---|---|
| tendonitis group | collagenase administration + normal feed | 10 |
| tendonitis + TAA group | collagenase administration + normal feed + TAA | 10 |
| tendonitis + TAA1 group | collagenase administration + normal feed + TAA1 | 10 |
| tendonitis + TAA2 group | collagenase administration + normal feed + TAA2 | 10 |
| tendonitis + TAA3 group | collagenase administration + normal feed + TAA3 | 10 |
| tendonitis + TAA4 group | collagenase administration + normal feed + TAA4 | 10 |
| tendonitis + TAA5 group | collagenase administration + normal feed + TAA5 | 10 |
| tendonitis + TAA6 group | collagenase administration + normal feed + TAA6 | 10 |

Figure 3:
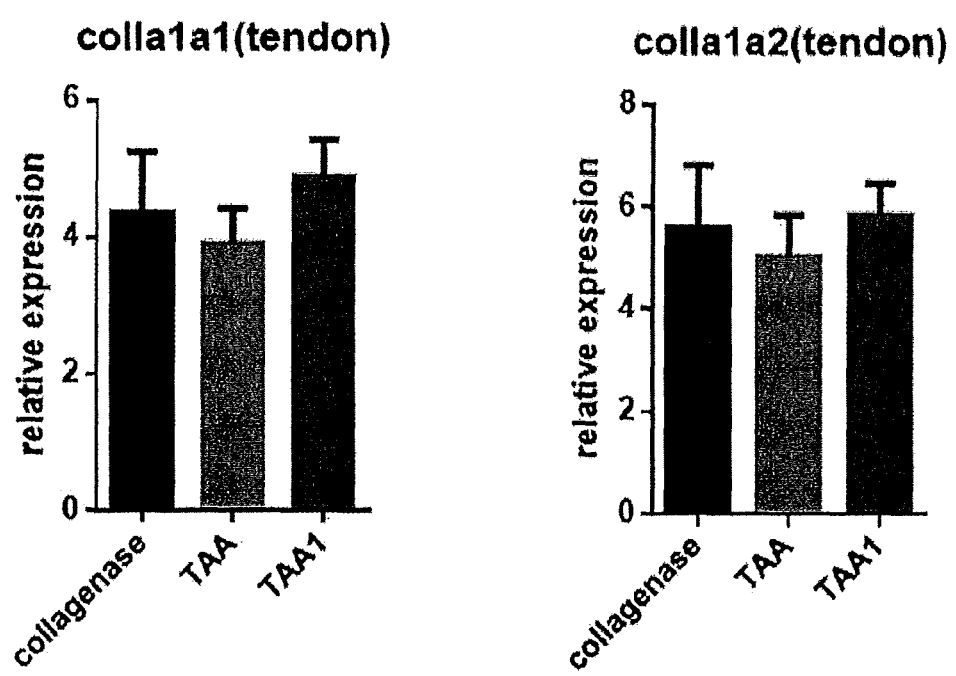
FIG. 3 shows the evaluation of the gene (tendon) on day 14 after the onset of tendonitis. Collagenase is a tendonitis group, and TAA or TAA1 is a group in which TAA or TAA1 was mixed with a feed and the mixture was given to a tendonitis model rat. The vertical axis shows a relative gene expression level.
Figure 4:
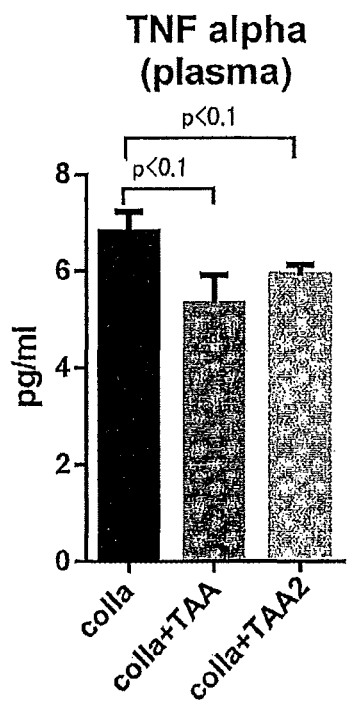
FIG. 4 shows the measurement results of plasma TNF-α concentration on day 14 after the onset of tendonitis. Colla is a tendonitis group, and colla+TAA or colla+TAA2 is a group in which TAA or TAA2 was mixed with a feed and the mixture was given to a tendonitis rat. The vertical axis shows a plasma TNF-α concentration.
Figure 5:
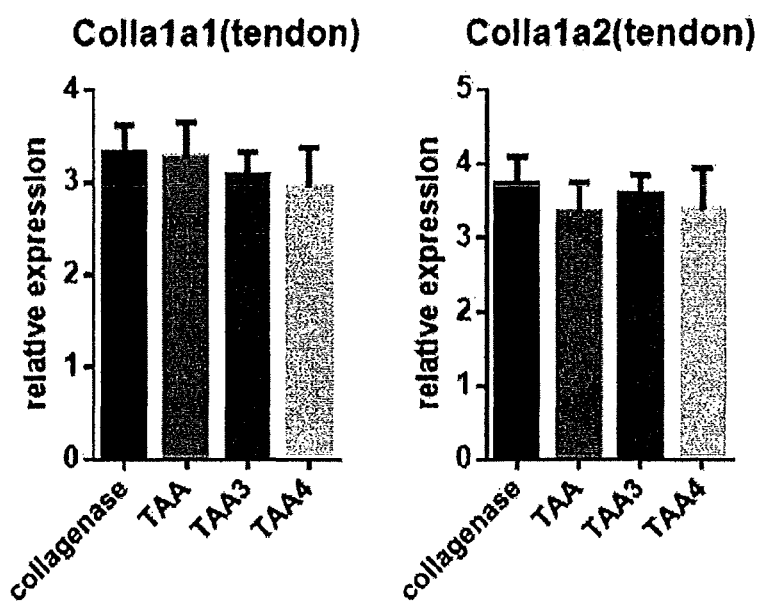
FIG. 5 shows the evaluation of the gene (tendon) on day 14 after the onset of tendonitis. Collagenase is a tendonitis group, and TAA is a group in which TAA was mixed with a feed and the mixture was given to a tendonitis rat. TAA3 or TAA4 is a group in which TAA3 or TAA4 was mixed with a feed and the mixture was given to a tendonitis rat.
Figure 6:
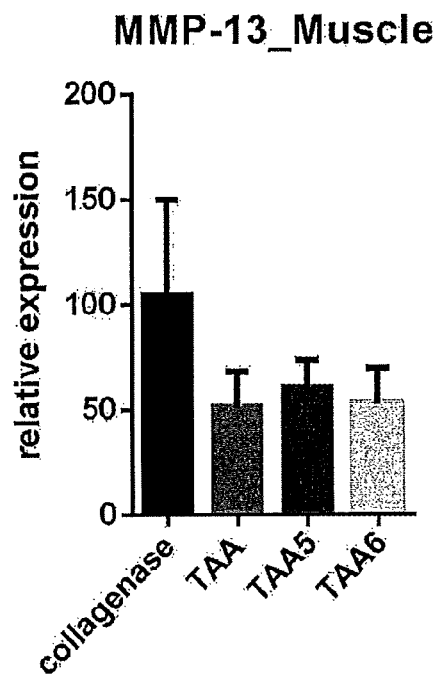
FIG. 6 shows the evaluation of the gene (muscle) on day 14 after the onset of tendonitis. Collagenase is a tendonitis group, and TAA is a group in which TAA was mixed with a feed and the mixture was given to a tendonitis rat. TAA5 or TAA6 is a group in which TAA5 or TAA6 was mixed with a feed and the mixture was given to a tendonitis rat. The vertical axis shows a relative gene expression level.

The results are shown in FIGS. 3 to 6. As shown in FIG. 3, TAA1 showed a gene expression effect equivalent to that of TAA in collagen synthesis. As shown in FIG. 4, TAA2 showed an anti-inflammatory effect equivalent to that of TAA. As shown in FIG. 5, TAA3 and TA4 showed a collagen synthesizing gene expression effect equivalent to that of TAA. As shown in FIG. 6, TAA5 and TAA6 showed a collagen degradation suppressive effect equivalent to that of TAA.

Example 4

Preparation of Osteoarthritis (OA) Model (1) OA group: 10-week-old male F344 rats (body weight 230 to 240 g) were anesthetized with isoflurane, the skin and fascia were longitudinally incised for about 3 cm, and patella bone was exposed. The anterior cruciate ligament in the joint cavity was cut with scissors. The patellar tendon was returned to the center, the skin was sutured with 4 or more stiches and the rats were returned to the cage.

(2) Sham group: skin and fascia were incised, sutured, and the rats were returned to the cage (Sham operation).

(3) The rats were normally bred during the 1 week recovery period.

(4) After the recovery period, a normal feed (16% casein-containing feed) was given to the sham group and the OA group, a mixed feed containing 2.34% (weight ratio) of amino acids at the proportion shown in Table 6 was given to the OS+TAA group and all groups were bred for 4 weeks. The amino acids other than alanine in Table 6 are L forms and all values are based on free form. The constitution of the groups is shown in Table 7.

(5) After breeding for 4 weeks, blood and cartilage were collected under anesthesia and anti-inflammation evaluation, collagen degradation evaluation and gene analysis were performed.

TABLE 6

| Ser | 0.3 |
|---|---|
| AspNa | 0.33 |
| Glu | 0.3 |
| Gly | 0.33 |
| D,L-Ala | 0.68 |
| Pro | 0.4 |

TABLE 7

| group | feed | n |
|---|---|---|
| Sham group | Sham ope + normal feed | 4-6 |
| OA group | OA ope + normal feed | 6-11 |
| OA + TAA group | OA ope + normal feed + TAA | 6-11 |

The results are shown in FIGS. 7 to 12 (test method: Dunnett's multiple comparisons test v.s. OA, *p<0.05. mean+SE, n=4-11).

Figure 7:
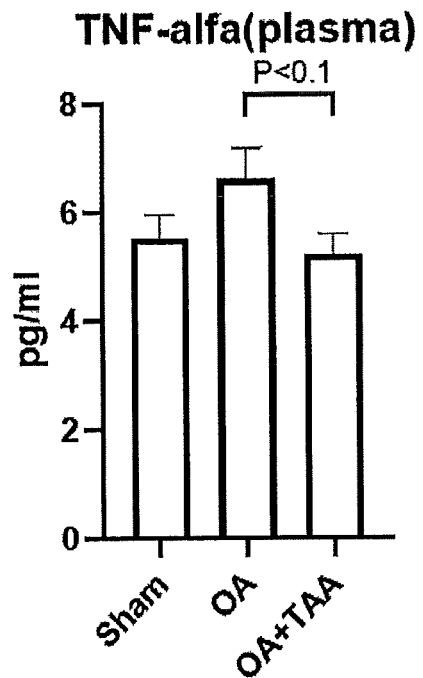
FIG. 7 shows the measurement results of the blood TNF-α concentration which is an inflammation marker in an osteoarthritis onset model. OA is an osteoarthritis group, Sham is a Sham operation group, OA+TAA is a group in which TAA was mixed with a feed and the mixture was given to an osteoarthritis model rat.
Figure 8:
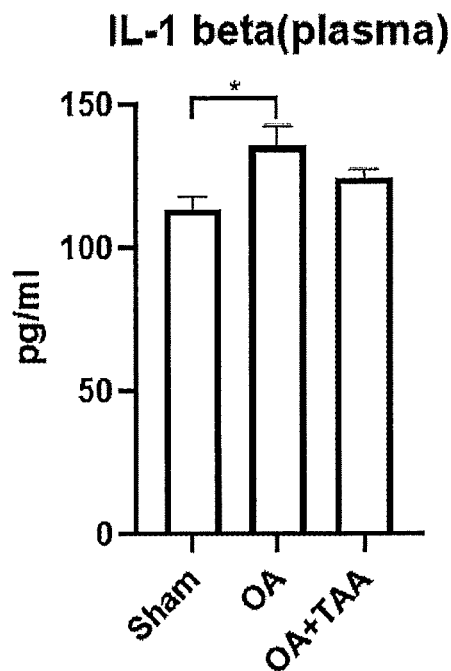
FIG. 8 shows the measurement results of the blood IL-1β concentration which is an inflammation marker in an osteoarthritis onset model. OA is an osteoarthritis group, Sham is a Sham operation group, OA+TAA is a group in which TAA was mixed with a feed and the mixture was given to an osteoarthritis model rat.

As shown in FIGS. 7 and 8, the inflammation markers blood TNF-α and IL-1β value increased in the OA group and decreased in the OA+TAA group. Therefore, inflammation was induced by OA ope and reduced by TAA.

Figure 9:
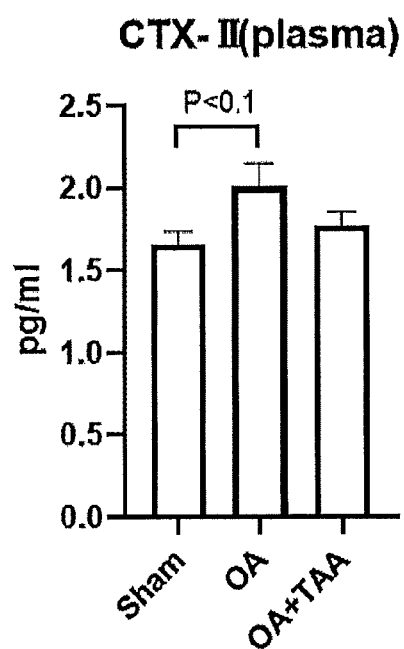
FIG. 9 shows the measurement results of the blood CTX-II concentration which is a cartilage collagen degradation marker in an osteoarthritis onset model. OA is an osteoarthritis group, Sham is a Sham operation group, OA+TAA is a group in which TAA was mixed with a feed and the mixture was given to an osteoarthritis model rat.

As shown in FIG. 9, the cartilage collagen degradation marker, blood CTX-II value, increased in the OA group and decreased in the OA+TAA group. Therefore, collagen degradation in cartilage was induced by OA ope and reduced by TAA.

Figure 10:
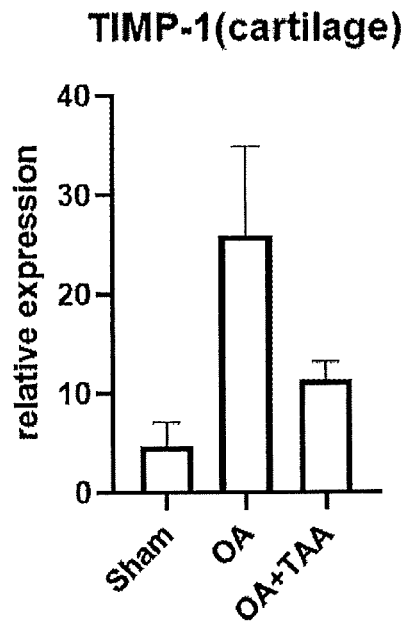
FIG. 10 shows expression of TIMP-1 gene which is an osteoclast formation marker in the cartilage tissue in an osteoarthritis onset model. OA is an osteoarthritis group, Sham is a Sham operation group, OA+TAA is a group in which TAA was mixed with a feed and the mixture was given to an osteoarthritis model rat.

As shown in FIG. 10, the expression of the osteoclast formation marker TIMP-1 gene in the cartilage tissue was promoted by OA ope and suppressed by TAA.

Figure 11:
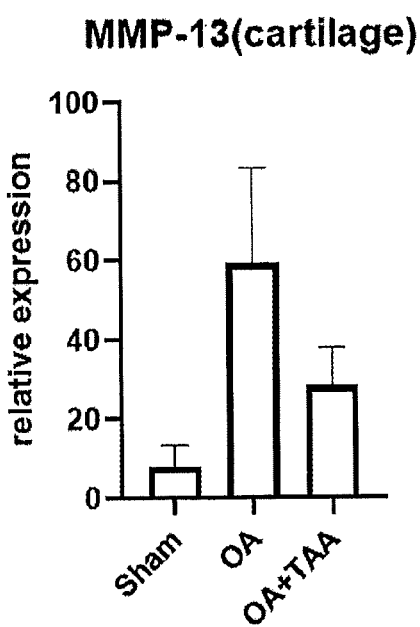
FIG. 11 shows expression of MMP-13 gene which is a collagen degradation enzyme in the cartilage tissue in an osteoarthritis onset model. OA is an osteoarthritis group, Sham is a Sham operation group, and OA+TAA is a group in which TAA was mixed with a feed and the mixture was given to an osteoarthritis onset model rat.

As shown in FIG. 11, the expression of the collagen degradation enzyme, MMP-13 gene, in the cartilage tissue was promoted by OA ope and suppressed by TAA.

Figure 12:
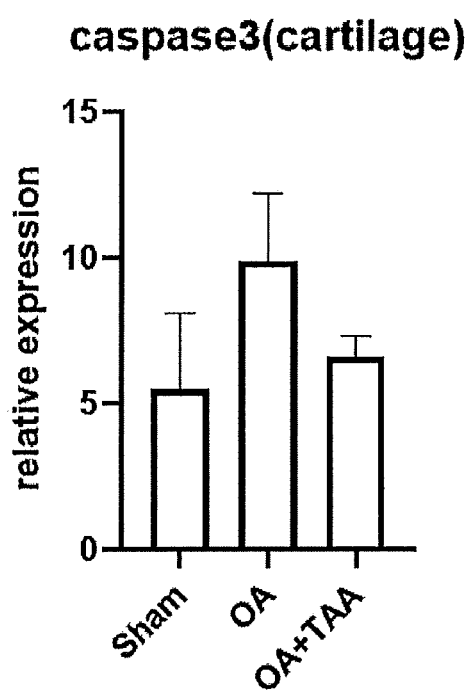
FIG. 12 shows expression of caspase3 gene which is an apoptosis-related enzyme in the cartilage tissue in an osteoarthritis onset model. OA is an osteoarthritis group, Sham is a Sham operation group, and OA+TAA is a group in which TAA was mixed with a feed and the mixture was given to an osteoarthritis onset model rat.

As shown in FIG. 12, the expression of the apoptosis-related enzyme, caspase3 gene, in the cartilage tissue was promoted by OA ope and suppressed by TAA.

The present invention can provide a composition effective for the improvement of injury and wear of cartilage in athletes and from children in the growth period to the elderly people.

INDUSTRIAL APPLICABILITY

The present invention can provide a composition effective for improving injury of joint such as tendon and ligament or functional decrease, strengthening joint function and prophylaxis of injury in athletes and from children in the growth period to the elderly people.

The present invention can provide a composition effective for improving articular disorders in pets and domestic animals due to aging, and prophylaxis or improvement of tendontis in racehorses.

The present invention can provide a composition effective for improving skin condition.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for improving joint function, consisting essentially of:
   administering a composition consisting of an effective amount of at least five kinds of amino acids selected from the group consisting of serine, aspartic acid, glutamic acid, glycine, alanine and proline as active ingredients to a subject in need thereof,
   wherein proportions of the at least five kinds of amino acids in the composition administered to the subject are 10 to 30 wt % of serine, 10 to 30 wt % of aspartic acid, 10 to 20 wt % of glutamic acid, 10 to 35 wt % of glycine, 10 to 30 wt % of alanine and/or 10 to 35 wt % of proline, relative to a total weight of serine, aspartic acid, glutamic acid, glycine, alanine and proline.

2. The method according to claim 1, wherein the improvement of joint function is improvement of joint disorder or prevention of joint disorder.

3. The method according to claim 2, wherein said joint disorder is at least one selected from the group consisting of tendonitis, patellar tendonitis, osteoarthritis, medial meniscus injury, osteochondritis dissecans, muscle strain, cartilage injury, tendon rupture, ligament injury, ligament rupture, lacertus injury, bone fracture, cartilage wear and loss of muscle strength caused thereby.

4. The method according to claim 1, wherein the improvement of joint function is joint strengthening.

5. The method according to claim 1, wherein the proportions of the at least five kinds of amino acids administered to the subject are 10 to 20 wt % of serine, 10 to 20 wt % of aspartic acid, 10 to 20 wt % of glutamic acid, 10 to 30 wt % of glycine, 10 to 25 wt % of alanine and/or 10 to 30 wt % of proline, relative to the total weight of serine, aspartic acid, glutamic acid, glycine, alanine and proline.

6. The method according to claim 1, comprising administering said serine, aspartic acid, glutamic acid, glycine, alanine and proline in a unit package form per serving for a human adult comprising 10 mg to 50 g in total of the said amino acids as active ingredients for single ingestion.

7. The method according to claim 1, wherein serine, aspartic acid, glutamic acid, glycine, alanine and proline are administered to the subject.

8. The method according to claim 1, wherein five kinds of amino acids selected from the group consisting of serine, aspartic acid, glutamic acid, glycine, alanine and proline are administered to the subject.

9. The method according to claim 3, wherein said joint disorder is at least one selected from the group consisting of tendonitis, patellar tendonitis, muscle strain, tendon rupture, ligament injury, ligament rupture, lacertus injury, bone fracture, and loss of muscle strength caused thereby.

10. The method according to claim 9, wherein said joint disorder is loss of muscle strength caused by tendonitis.

11. A method for improving joint function, consisting of:
    administering a composition consisting of an effective amount of at least five kinds of amino acids selected from the group consisting of serine, aspartic acid, glutamic acid, glycine, alanine and proline as active ingredients to a subject in need thereof,
    wherein proportions of the at least five kinds of amino acids administered to the subject are 10 to 30 wt % of serine, 10 to 30 wt % of aspartic acid, 10 to 20 wt % of glutamic acid, 10 to 35 wt % of glycine, 10 to 30 wt % of alanine and/or 10 to 35 wt % of proline, relative to a total weight of serine, aspartic acid, glutamic acid, glycine, alanine and proline.

12. The method according to claim 11, wherein the improvement of joint function is improvement of joint disorder or prevention of joint disorder.

13. The method according to claim 12, wherein said joint disorder is at least one selected from the group consisting of tendonitis, patellar tendonitis, osteoarthritis, medial meniscus injury, osteochondritis dissecans, muscle strain, cartilage injury, tendon rupture, ligament injury, ligament rupture, lacertus injury, bone fracture, cartilage wear and loss of muscle strength caused thereby.

14. The method according to claim 11, wherein the improvement of joint function is joint strengthening.

15. The method according to claim 11, wherein serine, aspartic acid, glutamic acid, glycine, alanine and proline are administered in a unit package form per serving for a human adult comprising 10 mg to 50 g in total of the said amino acids as active ingredients for single ingestion.

16. The method according to claim 11, wherein serine, aspartic acid, glutamic acid, glycine, alanine and proline are administered to the subject.

* * * * *